United States Patent
Dowling

(10) Patent No.: US 7,433,735 B2
(45) Date of Patent: Oct. 7, 2008

(54) MOTION SENSOR

(75) Inventor: Kenneth Dowling, Kungsängen (SE)

(73) Assignee: St. Jude Medical AB, Jarfalla (SE)

(*) Notice: Subject to any disclaimer, the term of this patent is extended or adjusted under 35 U.S.C. 154(b) by 486 days.

(21) Appl. No.: 10/532,790

(22) PCT Filed: Oct. 28, 2003

(86) PCT No.: PCT/SE03/01676

§ 371 (c)(1), (2), (4) Date: Apr. 25, 2005

(87) PCT Pub. No.: WO2004/039260

PCT Pub. Date: May 13, 2004

(65) Prior Publication Data

US 2006/0052832 A1 Mar. 9, 2006

(30) Foreign Application Priority Data

Oct. 31, 2002 (SE) .................. 0203220

(51) Int. Cl.
*A61N 1/00* (2006.01)

(52) U.S. Cl. ........................................ 607/19

(58) Field of Classification Search ............ 607/17–19; 73/702, 704, 705; 324/663
See application file for complete search history.

(56) References Cited

U.S. PATENT DOCUMENTS

| | | | | |
|---|---|---|---|---|
| 4,771,780 A * | 9/1988 | Sholder | ......... | 607/19 |
| 4,869,251 A | 9/1989 | Lekholm et al. | | |
| 5,233,984 A | 8/1993 | Thompson | | |
| 5,309,767 A * | 5/1994 | Parmar et al. | ......... | 73/705 |
| 5,755,741 A | 5/1998 | Vogel | | |
| 5,833,713 A | 11/1998 | Moberg | | |
| 2001/0048313 A1 * | 12/2001 | Frank | ......... | 324/663 |

* cited by examiner

*Primary Examiner*—George Manuel
(74) *Attorney, Agent, or Firm*—Schiff Hardin LLP

(57) ABSTRACT

A motion sensor, and an implantable cardiac stimulator incorporating such a motion sensor, has a fluid-type housing containing a fluid that includes at least one type of anisotropic molecules, the anisotropic molecules exhibiting an anisotropic property having a state that changes dependent on motion. The housing of the motion sensor is located externally on an animate subject, or is implanted in the animate subject, and includes externally accessible electrodes that detect a change in the state of the anisotropic property and emit an output signal representative of an activity level of the subject.

18 Claims, 2 Drawing Sheets

+- R ——————————————————————— R' +-

MOTION SENSOR

BACKGROUND OF THE INVENTION

1. Field of the Invention

The invention concerns a motion sensor for measuring a patient's activity level of the type having a fluid-tight, biocompatible housing, a number of electrodes coupled to the housing and the housing containing a fluid. Furthermore, the invention relates to an implantable cardiac pacemaker incorporating such a motion sensor.

2. Description of the Prior Art

Pacemakers are used to pace the beating frequency of the heart. They have been of greatest importance for helping individuals suffering from various heart diseases and/or failures to live rather normal lives. Pacemakers function by generating electrical pulses, which stimulate the heart. In order to pace the heart in a correct way, the specific pulse pattern of the individual heart must be known. It is advantageous to detect external parameters, such as the motion of the patient, in order for the pacemaker to stimulate the heart as correctly as possible.

Normally, the motion of the patient is measured by some kind of motion sensor, which is connected to the pacemaker. U.S. Pat. No. 5,755,741 discloses an implantable sensor providing an indication of movement and orientation of a patient. The sensor may be connected to a pacemaker. The sensor has a cylindrical enclosure having a central electrode within a cavity of the enclosure, and one or more peripheral electrodes within the cavity. An electrolytic fluid is positioned in the enclosure so that movement of the sensor results in variations of the amount of the fluid between the central electrode and one or more of the peripheral electrodes. An alternating current applied to the electrodes will produce an output voltage signal, which varies in accordance with the movements of the fluid (and the sensor).

U.S. Pat. No. 5,833,713 discloses an accelerometer-based, multi-axis physical activity sensor for use with a rate-responsive pacemaker. A piezoelectric polymer film is adhered to the surface of an electrically conductive substrate on the sensor. In response to bodily accelerations the piezoelectric film produces an output signal.

U.S. Pat. No. 5,233,984 discloses a multi-axis sensor, for example connected to a pacemaker, for measuring a patient's activity level. The sensor has a hermetically sealed, fluid-tight, biocompatible housing with a number of electrodes coupled to the sides of the housing, and a central electrode positioned within the housing. An electrically conductive electrolyte fills about half of the housing, allowing voltage changes, due to motion of the sensor, between the central electrode and the other electrodes to be monitored.

Also, U.S. Pat. No. 4,869,251 discloses a pacemaker having a sensor for detecting inertial and/or rotational movements of a patient. The sensor has a hollow member, with at least one freely moveable member therein generating a mechanical vibration upon movement of the patient. A transducer generates an electric signal corresponding to the mechanical vibrations. It is stated that the hollow member may be filled with a fluid and/or a number of particles producing pressure to the walls of the hollow member. It is also stated that the sensitivity of the sensor may be different in different directions. For example, the moveable element may be a magnetic dipole, and the transducer may be one or more coils arranged around the hollow member, whereby a current is generated in the coils when the moveable element changes position in the interior of the hollow member. Depending on configuration, however, the mobility of the movable element may degrade due to mechanical wear.

Such known motion sensors generally rely on moving mechanical components, and therefore they may be difficult to miniaturize further. This is a problem, because the size of the motion sensor (and pacemakers) advantageously is as small as possible, in order to disturb the biological system into which they are implanted as little as possible. Furthermore, as mentioned above, mechanically based sensors may suffer from mechanical wear, which can lead to their failure.

SUMMARY OF THE INVENTION

Accordingly, it is an object of the present invention to provide a motion sensor that overcomes the drawbacks of the prior art, and has as few mechanical parts as possible, as well as the sensor being as small as possible, and relying on a technical principle making it as resistant to failure as possible.

These and other objects are accomplished by a motion sensor according to the present invention, which relies on the principle of an electrically detectable anisotropic fluid, which fluid orients itself in relation to external motion.

A sensor thus is achieved employing no moving parts, and which therefore can be made very small.

In a preferred embodiment, the anisotropic fluid contains long, rigid LCP-molecules, on which electrically detectable magnetic nanoparticles are covalently linked.

In another embodiment a magnetic field is applied to the anisotropic fluid, and the alignment of the anisotropic molecules is detected by measuring the capacitance of the fluid.

In yet another embodiment an electrostatic field is applied to the anisotropic fluid, and the alignment of the anisotropic molecules is detected by measuring the capacitance of the fluid.

Moreover, the invention relates to an electrically detectable anisotropic fluid comprising a liquid crystalline polymer (LCP) as the anisotropic fluid, which LCP is covalently bound to an iron-oxide nanoparticle. This fluid is specifically suitable for use in the motion sensor of the invention.

Furthermore, the invention relates to an implantable pacemaker incorporating the motion sensor of the invention. A patient's heart is paced as a response to the patient's motion, sensed by the motion sensor of the invention.

Accordingly, the drawbacks of the prior art are overcome.

DESCRIPTION OF THE PREFERRED EMBODIMENTS

Figure 1:
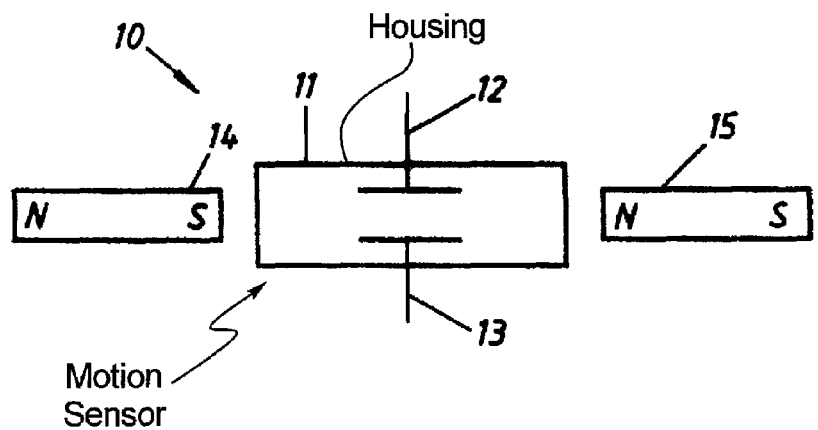
FIG. 1 is a block diagram of a motion sensor according to one embodiment of the invention.

An aim of the invention is to provide a motion sensor, especially adapted for use with a pacemaker, which is as small as possible, and which circumvents the problem of mechanical wear in a sensor comprising several mechanical parts. This is accomplished by a sensor that relies on the principle of an anisotropic fluid or an anisotropic molecule within a fluid. Thus, the only moving parts of the sensor are fluids.

In accordance with the invention a motion sensor for measuring a patient's activity level has a fluid-tight, bio-compatible housing, a number of electrodes coupled to the housing, and the housing contains a fluid that includes at least one anisotropic molecule, the anisotropic properties of which change in relation to the motion of the fluid, so the state of the anisotropic molecules of the fluid is detectable by the electrodes.

In a preferred embodiment, the motion sensor is implantable in a patient. The motion sensor alternatively may be adapted for external use, i.e. not being implanted in the body of the patient, but communicating with an implanted pacemaker, such as by telemetry.

The term "patient" as used herein means an animal, especially a human, in need of a motion sensor. This may include, for example, persons having a pacemaker or who are to be equipped with a pacemaker. The motion sensor of the invention, however, need not necessarily be coupled to a pacemaker, but may be connected to any other device or circuitry for which the output of the motion sensor is relevant.

As used herein, a patient's "activity level" means the degree of motion for the specific patient. For example, for a pacemaker to deliver the correct pulses to a patient's heart, it is important to correlate these pulses with the "activity level" of the patient, in order for the pacing pulses and the resulting heart responses to be suited for the patients present need. Thus, it is preferred that the paced heart rate is adaptable to different levels of exertion by the patient.

As used herein, "a number of electrodes" means at least one electrode pair, having the capacity to monitor at least one electronic parameter.

An anisotropic molecule will orient itself in relation to motion-caused forces to which it is subjected. Thus, for example, an anisotropic molecule may exhibit anisotropic properties at rest and isotropic properties when agitated (i.e. different states). Accordingly, a number of molecules of this kind will, like a crystal, align in a common direction at rest, or in a laminar shearing force. The viscosity, as well as several other physico-chemical properties, such as optical transmission, heat transfer, polarity, conductivity etc., will then be very different in the alignment direction compared to other directions, especially the perpendicular direction. However, if agitated, the molecular alignments will become random, and as a result properties such as viscosity or dielectric constant will be practically equal in all directions. Thus, when a patient carrying the sensor of the invention moves, the sensor will sense these movements (or lack of movements) and create an output signal dependent on the movements.

Liquid crystalline polymers (LCP's)(Langmuir 2001, 17, 2900-2906) are fluids having anisotropic properties at rest and isotropic properties during agitation. LCP's, in the context of the invention, are long rigid molecules, which have an aspect-ratio (length/diameter) of greater than about (10/1). One example, which is suitable for the purposes of the invention, is poly-(p-phenylene) with a degree of polymerization (n) equal to or greater than 10. In this context, the aspect-ratio would be a more relevant term than for example molecule length, since a rigid rod polymer with a wide diameter will not exhibit anisotropic properties at the same length or degree of polymerization as a rigid rod polymer with a narrow diameter. The aspect-ratio, however, provides a good way to measure the intrinsic anisotropy of the polymer molecules.

Thus, according to one embodiment of the invention the anisotropic molecule is a liquid crystalline polymer (LCP).

Some other examples of liquid crystalline polymers suitable for the invention are given below. However, this list is not exhaustive, and other compounds may also be used.

A copolymer of p-hydroxybenzoic acid and polyethylene terephthalate. (Japanese Patent Publication No. 18016/1981); a copolymer of p-hydroxybenzoic acid, polyethylene terephthalate, aromatic diol (such as 4,4'-dihydroxybiphenyl), and aromatic dicarboxylic acid, with improved flowability and heat resistance. (Japanese Patent Laid-open No. 30523/1988); a copolymer of p-hydroxybenzoic acid, 4,4'-dihydroxybiphenyl, t-butylhydroquinone, and terephthalic acid. (Japanese Patent Laid-open No. 164719/1987); a copolymer of p-hydroxybenzoic acid, 4,4'-dihydroxybiphenyl, isophthalic acid, and terephthalic acid. (Japanese Patent Publication No. 24407/1982 and Japanese Patent Laid-open No. 25046/1985); a copolymer of p-hydroxybenzoic acid and 6-hydroxy-2-naphthoic acid. (Japanese Patent Laid-open No. 77691/1979); copolyesters of terephthalic acid, alkylhydroquinone, p-hydroxybenzoic acid and poly(alkylene terephthalate), the alkylene substituent preferably containing ethylene or butylene and the alkyl substituent of the hydroquinone preferably containing a lower alkyl group such as propyl or (tertiary) butyl; copolyesters of p-hydroxybenzoic acid and poly(alkylene terephthalate), the alkylene group preferably being ethylene or butylene; copolyesters of terephthalic acid, alkylhydroquinone, p-hydroxybenzoic acid and hydroxyalkylphenyl-alkanoic acids, the alkyl-substituent of the hydroquinone preferably containing a lower alkyl group such as propyl or (tertiary) butyl, the alkanoic acid preferably containing 3 to 8 carbon atoms, propanoic acid being particularly preferred, and blockcopolyesters of trimellithic imide-terminated poly(THF) or polysilicone, containing the imide group in para- or meta-position i.e. N-(4-carboxy-phenyl)-trimellit imide or N-(3'-acetoxy-phenyl)-trimellit imide, with acetoxybenzoic acid and at least one repeating unit selected from the group including diacetoxy diphenyl, hydroquinone diacetate, terephthalic acid, a trimer designated HBA-HQ-HBA (the synthesis of which is described in Europ. Polym. J. 20, 3, 225-235 (1984), and poly(ethylene terephthalate) (PET).

The molecular weight of the liquid crystal polymer used in the present invention depends on the character of the repeating units of the LCP. Usually, the molecular weight is in the range of about 1,000 to 300,000. If fully aromatic polyesters are used as LCP's, their molecular weight is typically in the range of about 2,000 to 200,000, preferably about 10,000 to 50,000.

More general details on liquid crystalline polymers and their properties and applications are given in an article titled "Liquid Crystal Polymers and Their Applications" by Chung et al. in Handbook of Polymer Science and Technology, Vol. 2 (1989) 625-675.

In order to be able to detect the anisotropic properties a doping agent, for example, may be attached to the anisotropic molecule, the doping agent having the capacity to provide a readable electronic signal. Thus, the doping agent constitutes an electrically detectable component allowing a patient's activity level to be monitored.

The doping agent is coupled to the LCP-molecule by any common chemical bonding technique. Preferably, the doping agent is coupled to the LCP-molecule by covalent bonding. Those skilled in the art are familiar with techniques for binding the doping agent to the LCP, e.g. by hydrosilylation reactions using organosilane intermediates, for example dimethylvinyl silane.

Therefore, according to another embodiment the anisotropic molecule includes an electrically detectable component.

The production of silica-coated iron oxide nanoparticles is described in the reference article Langmuir, Vol 17, No. 10, 2001 (2900-2906). Basically, they are produced in solution from appropriate chemical reagents, aided by suspension in organic surfactants. The particles are treated with tetraethylorthosilicate (TEOS) to form a silica coating. These particles are magnetic, and can be bound to an isotropic (rigid rod) molecule using covalent bonding and standard silica surface treatment chemistry, for example by silanization with dimetylvinyl silane. In one embodiment of the present invention, the silane group bonds to the silica surface, and the vinyl group can form a covalent bond with many different kinds of organic molecules, including Liquid Crystalline Polymers (LCP's) containing dipoles. Under a small magnetic field (B), such as greater than about 0.5 Gauss, a preferential orientation will be induced, so that the magnetic particles line up in the magnetic field. The degree of alignment is preferably detected by measurement of capacitance across the fluid. The tendency for alignment is dependent on agitation because the dipoles will be forced by the magnetic particles to line up in the preferential orientation, but that orientation is disturbed by fluid motion.

A basic illustration of one embodiment of the motion sensor of the invention is shown in FIG. 1. The sensor 10 has a housing 11, which is filled by a fluid. At least a part of the fluid is anisotropic molecules of the invention. Furthermore, a magnetic field is generated by the magnets 14 and 15. The fluid forms a capacitor with electrodes 12 and 13 the capacitance of which can be measured, and thus a variation in the anisotropic status of the fluid is monitored.

Examples of doping agents are ions or molecular dipoles. Preferably, a magnetically aligned nanoparticle (Langmuir 2001, 17, 2900-2906), or a charge-separated ion-pair, such as a zwitterionic pair (positive charge at one end, negative at the other) is used. The nanoparticle is in a preferred embodiment an iron-oxide nanoparticle, wherein iron-oxide may be represented by e.g. $Fe_3O_4$, or $\gamma$-$Fe_2O_3$ (Langmuir 2001, 17, 2900-2906)

Thus, in another embodiment of the invention the detectable component is a magnetic nanoparticle, a zwitterionic pair or a charge separated ion-pair, preferably a magnetic iron-oxide nanoparticle.

In one preferred embodiment, the anisotropic fluid contains long rigid LCP-molecules, on which electrically detectable charge-separated ion pairs are covalently linked.

In another embodiment an electric field is applied to the anisotropic fluid, and alignment of the anisotropic molecules is detected by measuring the capacitance of the fluid.

Moreover, the invention relates to an electrically detectable anisotropic fluid comprising a LCP as the anisotropic fluid, which LCP is covalently bound to two charge-separated ion pairs of different charge at each end of the LCP rigid rod.

In a non-polar medium such as an LCP fluid, ions are associated with other ions of opposite charge, forming an ion pair. One ion pair alone is sufficient to cause orientation in an electric field. However, a very strong field would be required to align long rod LCPs if only one ion pair were attached at one end. Consequently, it is preferable to have two different ion pairs at each end (one must be a negative group covalently bond, such as a carboxylate ion R—$COO^-$ with counter-ion $Na^+$, and the other a positive ionic group such as R'—$NH_3^+$ with counter-ion $Cl^-$). Choices of the covalently bonded ion and its counter-ion are many, and any choice that is suitable for use in the present invention may be chosen. A "zwitterion" is the name for any molecule containing two such ionic groups of opposite charge as described above and illustrated in FIG. 3.

In an electrostatic field, as is created between capacitor plates of opposite charge (FIG. 4), the charges on the LCP pictured above will cause the rigid rod to readily align itself in the field, creating anisotropy behavior in the many properties of the fluid, including (but not limited to) viscosity, resistance, dielectric constant, etc. A very low electrical field strength (E) may be possible to facilitate the alignment, preferably E less than 1 V/m. Agitation of the fluid causes temporary randomization of orientation which is easily detected in a number of ways as discussed previously for the magnetic particle doped materials. At rest, the anisotropy is restored to the fluid due to the influence of the electrical field aligning the ion pairs of these zwitterionic molecules. The viscosity, as well as other physico-chemical properties, such as optical transmission, heat transfer, polarity, conductivity, etc., will then be different in the alignment direction compared to other directions, especially the perpendicular direction.

Figures 3, 4:
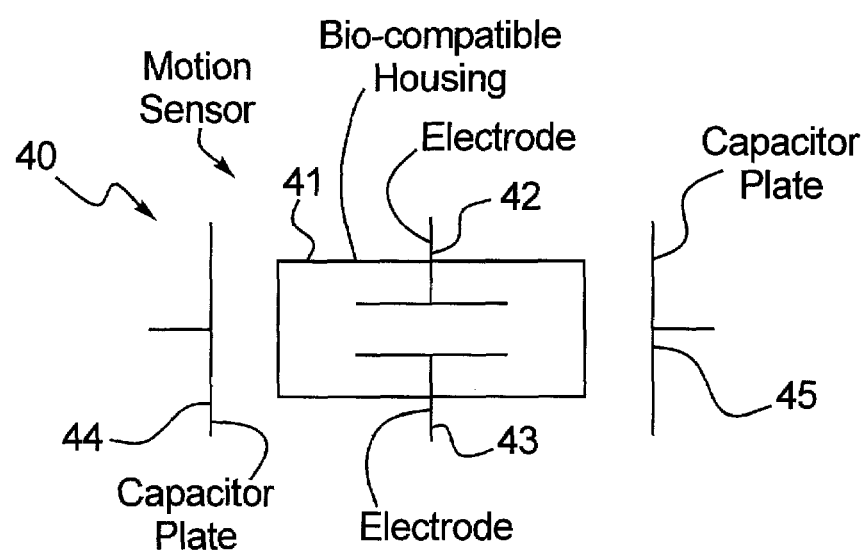
FIG. 3 shows a zwitterion.
FIG. 4 is a block diagram of a motion sensor according to another embodiment of the invention.

FIG. 4 illustrates this embodiment. A motion sensor 40 has a biocompatible housing 41 and electrodes 42 and 43. Positively and negatively charged capacitor plates, 44 and 45, respectively, are used to align the LCP-molecules in the housing.

Those skilled in the art (of combinatorial organic chemistry, for example) are familiar with techniques for binding the doping agent to the LCP, e,g, by hydrosilylation reactions involving organosilane intermediates, for example dimethylvinylsilane, which leaves a vinyl group for binding e.g. organic acid and base groups such as —R—$COO^-$ and —R'—$NH_3^+$ where R and R' are any organic moiety containing a vinyl group.

A reason for the use of a zwitterionic or charge-separated ion pair as a dopant on the LCP-molecule, and the use of an electrostatic field (such as between capacitor plates) for alignment of the LCP-molecules, is that it is desirable to avoid disturbances of the function of a pacemaker from external magnetic fields, and this need is met by this embodiment.

The electrical/magnetic signature is representative of the degree of alignment of the LCPs. As a consequence, the amount of agitation (i.e. patient activity) is correlated to the electrical or magnetic signal, which the sensor and/or pacemaker circuitry is designed to detect. As a result a motion sensor having no moving parts (except the anisotropic fluid) and that can be made very small can be manufactured. For example, the sensor may have a cavity volume of a few $mm^3$ or less, such as less than 10 $mm^3$, preferably less than 5 $mm^3$, most preferably less than 1 $mm^3$.

The suitable electronic signal to be monitored may vary depending on the nature of the system and its chemical content. However, for many applications measure of capacitance is suitable. In other cases measurement of voltage, voltage changes, impedance or resistance may be suitable.

Thus, in another embodiment the state of the anisotropic molecule is monitored by measuring the capacitance of the fluid.

In another embodiment the state of the anisotropic molecule is monitored by measuring the resistance of the fluid.

In another embodiment, coils are arranged around the housing. Upon a variation in the state of the anisotropic fluid, a voltage is induced in the coils, which voltage is used as a signal. For example, the coil may be of insulated silver/copper wire.

The nanoparticulate size of the anisotropic entity molecules enables low enough viscosity that no moving parts (other than fluid) is necessary, even in small devices like a pacemaker. A half-empty cylinder is one preferred example of the container. This container preferably has a magnetic N and a magnetic S pole provided by placement of permanent magnets 14 and 15 on opposite sides of its diameter. The electric sensor (e.g. capacitor electrodes 12 and 13) may also be on opposite sides of the cylinder diameter, though preferably normal (90 degrees) to the magnetic diameter (see FIG. 1).

It is not required to have the capacitor electrodes normal to the magnetic field, but it provides the optimum signal output. Each molecule of the fluid will act as a dipole with a dipole moment in a particular direction. When in a magnetic field, the dipole moments will tend to align in due to being bound to the magnetic particles as described in the reference article. The net dipole moment of the fluid is then finite and detectable as capacitance between the capacitance electrode. This "high order state" is detectable across any plane of the fluid except that parallel to the magnetic field, since in the parallel plane the LCP molecule ends face the electrodes and the LCP fluid would appear to the sensor to be small molecules with no preferable orientation in that plane. Therefore, in the "high order state", the signal is obtained as long as the capacitor electrodes are not in the parallel plane, a detectable signal in any other plane, and an optimum signal is obtained in the perpendicular plane. Note that when agitated, the dipoles become randomly oriented yielding a much lower net dipole moment—this "low order state" gives the same signal output independent of orientation between the capacitor electrodes and the magnetic field. So to achieve the maximum difference between the "at rest" state (high order) and the active state (low order), perpendicular is the preferred set-up, but sensitive electronics means that any orientation other than parallel to the magnetic field suffices.

However, in another embodiment an anisotropic molecule exhibiting a specific dipole moment even in the parallel plane is used.

In the invention, air is preferably used as the agitating medium. However, it is also possible to have a completely filled cavity if it is ensured that the anisotropic fluid is agitated with body motion (note, it is fluid agitation that results in its altered properties). One such embodiment is a flexible housing completely filled, whereby the motion of the housing provides the agitation. Another embodiment would be to have a completely filled cavity containing inert particles in the fluid, which agitate the fluid with body motion (kind of like the ball bearing in spray-paint cans). If air is the agitator (which is preferred), 98% fluid is a reasonable upper limit. As a lower limit, enough fluid to fill the space between electrodes (preferably capacitor plates) is needed, which would necessitate a lower limit of about 20% fluid.

It is important that the sensor be implantable in the human body so the sensor is preferably constructed of biocompatible material. Furthermore, since the housing of the sensor contains a fluid, it is important that the housing be entirely fluid-tight, in order to assure the function of the sensor as well as no risk of harm of the patient.

The housing may be formed, for example, of glass, ceramic, Plexiglas®, thermoplastic, curable plastic, metal, rubber (for example silicone rubber) or any other suitable material. Also, the housing may be formed of any conventional structural biocompatible dielectric material, such as ceramic, phenolic resin, epoxy resin or polysulfone. The shape of the housing may for example be spherical, cylindrical, cubical, of a horseshoe-shaped annulus form, or any other functional shape.

In one embodiment, the housing is configured in the shape of a cube having six sides, and the electrode includes six generally identical rectangularly shaped side electrodes. Each of these side electrodes is coupled to one side of the housing. The electrodes are electrically accessible outside of the sensor via conventional feed-throughs.

The electrodes can assume different shapes, such as a rectangle, a circle, a triangle, a parabola, or such other geometric shapes that will enable the mapping of the voltages, voltage changes, impedances and impedance changes between various reference points on the side electrodes.

These side electrodes are composed of conventional conductive material such as stainless steel or titanium. The side electrodes may be supported remotely by feed-through connector wires or may be connected to the side via an insulator.

In another embodiment shear forces acting on in the anisotropic fluid are produced by using a solid mechanical moveable element, such as a bead or a ball made of non-ferromagnetic metal, contained in the housing.

The sensitivity of the sensor can be varied by varying the concentration of the anisotropic molecule in the fluid.

The sensitivity of the sensor may also be varied by varying the viscosity of the fluid in the housing.

The invention also encompasses an electrically detectable anisotropic fluid containing a liquid crystalline polymer (LCP) as the anisotropic fluid, which LCP is covalently bound to an iron-oxide nanoparticle. Thus, a fluid is provided that is specifically adapted for use in a motion sensor of the invention.

The invention also encompasses an implantable cardiac pacemaker incorporating the implantable motion sensor described above, and means for pacing a heart, such as a pulse generator, as a response to the activity level as detected by the motion sensor, which means is connected to said motion sensor. The physical activity of the patient in which the pacemaker is implanted is monitored using the sensor, and the output signal of the sensor is used to control the frequency of the pulse generator.

In an alternative embodiment of this aspect, the pacemaker does not contain the motion sensor itself, but contains a unit for receiving signals from an external motion sensor. In this case, the external motion sensor communicates by means of telemetry or the like with the pacemaker.

As used herein "implantable pacemaker" means a pacemaker that can be safely implanted in a patient, and thus the pacemaker should be constructed of biocompatible material.

The term "means for pacing a heart" means any kind of conventional pacemaker or pulse generator, such as implantable cardiac defibrillators, such as Microny® or Regency®. Those skilled in the art know suitable devices for use for this purpose.

In one embodiment, the sensor forms an entirely self-contained system within the heart pacemaker, which requires no additional external detectors or line connections outside of the heart pacemaker housing.

In another embodiment, the sensor can be implanted independently, remotely from the implanted medical device. Yet another alternative is to have the patient wear the sensor externally, such that the output signals from the sensor are transmitted by telemetry to the implanted medical device.

In any case, the sensor should be as small as possible, e.g. to allow incorporation into an implantable pacemaker, preferably 0.5 cm square, or less.

In a preferred embodiment the output signal is capacitance, which must first be converted to a voltage signal. The sensor response frequencies need to be calibrated to correspond with appropriate patient motion frequencies.

Figure 2:
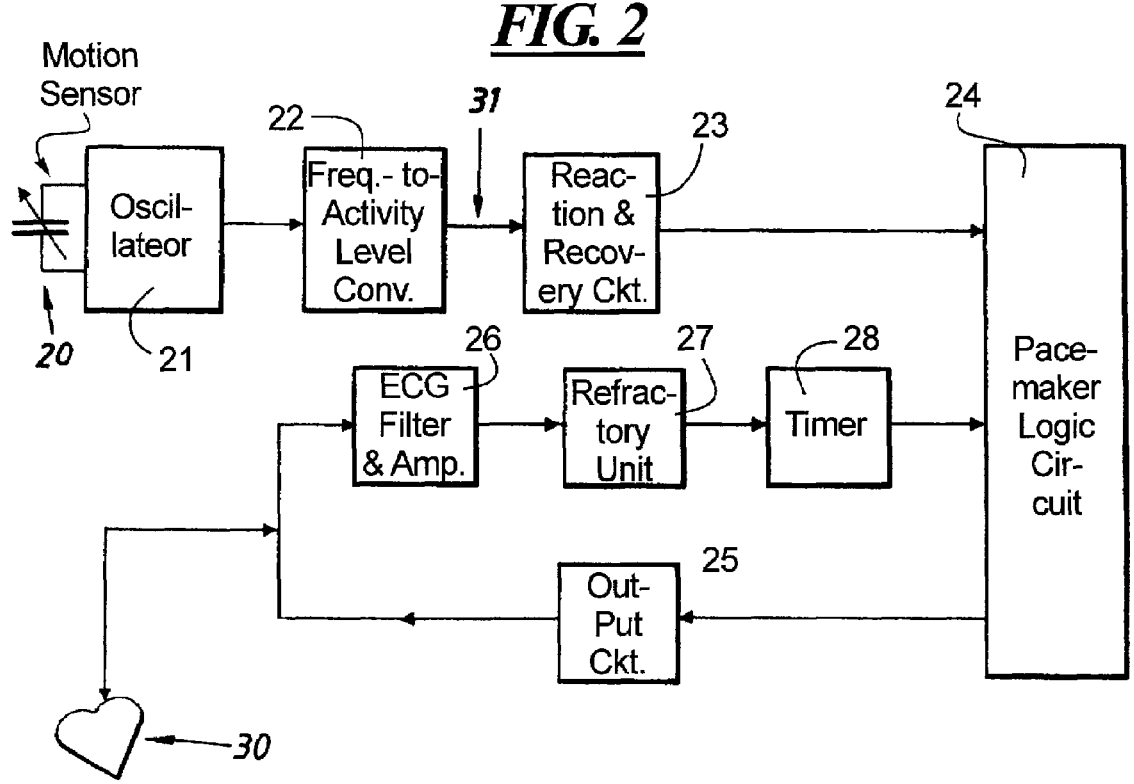
FIG. 2 is a block diagram of a rate response pacemaker accordingly to the present invention, incorporating a motion sensor according to the present invention.

The use of a sensor of the present invention in combination with control circuitry for a heart pacemaker may be as follows (FIG. 2): The sensor 20 according to this embodiment of the invention contains a fluid, whose properties of dielectric permittivity change when agitated, causing a corresponding change in the capacitance between two electrodes (as described above). The variable capacitance is used as an input signal to an oscillator 21, which produces an output frequency that depends on the capacitance input. The frequency generated by the oscillator 21 is processed and converted to an appropriate signal in a frequency-to-activity-signal converter 22, as is known in the art. The signal from the converter 22 is combined with input of a programmable target rate 31 and is further processed in a reaction and recovery circuit 23 to ensure appropriate reaction time and recovery time of the stimulation to the detected activity signals. The remaining components are standard and known to those skilled in the art of rate-responsive cardiac pacing. Those components include a pacemaker logic circuit 24, an output circuit 25, an ECG (electrocardiogram) filter and amplifier 26, a refractory unit 27, and a timer 28 for the highest inhibited rate. The total circuit is coupled to the heart 30 of a subject between the output circuit 25 and the ECG filter and amplifier 26. Reference is made to e.g. U.S. Pat. No. 5,233,984 and to Lindgren and Jansson, "Heart Physiology and Stimulation, an introduction", 1992, Siemens-Elema AB, Solna, Sweden.

The control signal for the heart pacemaker may be generated in digital form instead of the analog format discussed above. Digital processing can be undertaken in a microprocessor. In both cases, the programming can be done via a telemetry link between the heart pacemaker and an external programming means.

In one embodiment of the invention a low/high frequency band pass filter (for measuring a patient's posture and activity) is used. This filter preferably is calibrated, since the fluid properties of the fluid of the sensor will affect sensor response frequencies. Filtering frequencies may therefore need adjustment.

Although modifications and changes may be suggested by those skilled in the art, it is the invention of the inventor to embody within the patent warranted heron all changes and modifications as reasonably and properly come within the scope of his contribution to the art.

I claim as my invention:

1. A motion sensor for measuring an activity level of an animate subject, comprising:
    a substantially non-deformable fluid-tight housing configured for placement relative to a subject for co-movement with movements of the subject;
    a fluid contained in said housing, said fluid comprising at least one type of anisotropic molecules, having an anisotropic property that changes dependent on motion of said fluid imparted to said fluid exclusively by the co-movement of said housing with said movements of said subject; and
    electrodes in communication with said anisotropic molecules that detect a state of said anisotropic property, said electrodes being accessible from an exterior of said housing to provide an output signal representing an activity level of the subject.

2. A motion sensor as claimed in claim 1 wherein said housing is comprised of biocompatible material, and is adapted for implantation in the subject.

3. A motion sensor as claimed in claim 1 wherein said anisotropic molecules comprise a liquid crystalline polymer.

4. A motion sensor as claimed in claim 3 wherein said liquid crystalline polymer is poly (p-phenylene) having a degree of polymerization equal to or greater than 10.

5. A motion sensor as claimed in claim 1 wherein said anisotropic molecules comprise an electrically detectable component.

6. A motion sensor as claimed in claim 5 wherein said electrically detectable component is covalently coupled to said anisotropic molecules.

7. A motion sensor as claimed in claim 5 wherein said electrically detectable component is selected from the group consisting of magnetic nanoparticles, zwitterionic pairs, and charge-separated ion pairs.

8. A motion sensor as claimed in claim 5 wherein said electrically detectable component comprises iron oxide nanoparticles.

9. A motion sensor as claimed in claim 1 comprising a magnetic field source disposed externally of said housing that generates a magnetic field that interacts with said anisotropic molecules to cause said anisotropic property to be in an initial state, and wherein said electrodes detect deviation of said anisotropic property from said initial state.

10. A motion sensor as claimed in claim 9 wherein said anisotropic property is capacitance, and wherein said electrodes comprise a pair of capacitor electrodes with said fluid disposed therebetween, said capacitor electrodes being oriented perpendicularly to an applied direction of said magnetic field.

11. A motion sensor as claimed in claim 1 comprising a electrostatic field source disposed externally of said housing that generates a electrostatic field that interacts with said anisotropic molecules to cause said anisotropic property to be in an initial state, and wherein said electrodes detect deviation of said anisotropic property from said initial state.

12. A motion sensor as claimed in claim 1 wherein said anisotropic property is capacitance, and wherein said electrodes detect the capacitance of said fluid.

13. A motion sensor as claimed in claim 1 wherein said anisotropic property is resistance, and wherein said electrodes detect the resistance of said fluid.

14. A motion sensor as claimed in claim 1 wherein said housing contains an element interacting with said fluid that produces shear forces in said fluid that alters said anisotropic property of said molecules.

15. An electrically detectable anisotropic fluid comprising a liquid crystalline polymer having molecules covalently bound to an iron-oxide nanoparticle.

16. A cardiac stimulator comprising:
    a motion sensor that measures an activity level of an animate subject comprising a substantially non-deformable fluid-tight housing configured for placement relative to a subject for co-movement with movements of the subject, a fluid contained in said housing, said fluid comprising at least one type of anisotropic molecules, having an anisotropic property that changes dependent on motion of said fluid imparted to said fluid exclusively by the co-movement of said housing with said movements of said subject, and electrodes in communication with said anisotropic molecules that detect a state of said anisotropic property, said electrodes being accessible from an exterior of said housing to provide an output signal representing an activity level of the subject;
    a stimulator housing configured for implantation in the subject;
    stimulation circuitry contained in said stimulator housing that generates electrical stimulation therapy signals;
    an electrode system configured for implantation in the subject, said electrode system being connected to said stimulation generator and being configured to interact with tissue in the subject to deliver said electrical stimulation therapy; and a control unit in said stimulator housing connected to said stimulation generator, and being in communication with said motion sensor to receive said output therefrom representing said activity level, said control unit modifying said electrical stimulation therapy dependent on said activity level.

17. A cardiac stimulator as claimed in claim 16 wherein said housing of said motion sensor is contained in said stimulator housing.

18. A cardiac stimulator as claimed in claim 16 wherein said stimulation generator comprises a pacing pulse generator.

* * * * *